United States Patent [19]

Fuchs et al.

[11] 4,136,162

[45] Jan. 23, 1979

[54] MEDICAMENT CARRIERS IN THE FORM OF FILM HAVING ACTIVE SUBSTANCE INCORPORATED THEREIN

[75] Inventors: Peter Fuchs; Jürgen Hilmann, both of Berlin, Germany

[73] Assignee: Schering Aktiengesellschaft, Germany

[21] Appl. No.: 865,080

[22] Filed: Dec. 27, 1977

Related U.S. Application Data

[63] Continuation of Ser. No. 803,328, Jun. 3, 1977, abandoned, which is a continuation of Ser. No. 591,634, Jun. 30, 1975, abandoned.

[30] Foreign Application Priority Data

Jul. 5, 1974 [DE] Fed. Rep. of Germany ....... 2432925
Oct. 17, 1974 [DE] Fed. Rep. of Germany ....... 2449865

[51] Int. Cl.$^2$ .................... A61K 9/70; A61K 31/70; A61K 31/74
[52] U.S. Cl. .................... 424/27; 424/28; 424/78; 424/180
[58] Field of Search .................... 424/27, 28, 78, 180

[56] References Cited

U.S. PATENT DOCUMENTS 3,449,489   6/1969   Gaunt .................... 424/31

FOREIGN PATENT DOCUMENTS 163525    6/1955   Australia.
413446    5/1969   Australia.
1543770  11/1971   Australia.

Primary Examiner—Stanley J. Friedman
Assistant Examiner—D. W. Robinson
Attorney, Agent, or Firm—Millen & White

[57] ABSTRACT

Pharmaceutical composition unit dosage forms adapted for enteral or topical administration are described, comprising a safe and effective amount of a pharmaceutically active medicament compound dissolved or uniformly dispersed in a flexible, water-soluble film carrier therefor. Admixtures of medicament and carrier are drawn into a film, which can be cut to desired unit dosage content.

16 Claims, No Drawings

MEDICAMENT CARRIERS IN THE FORM OF FILM HAVING ACTIVE SUBSTANCE INCORPORATED THEREIN

This is a continuation of application Ser. No. 803,328, filed June 3, 1977, now abandoned, which in turn is a continuation of Ser. No. 591,634 filed June 30, 1975 abandoned.

BACKGROUND OF THE INVENTION

This invention relates to pharmaceutical compositions in unit dosage form comprising a pharmaceutically active medicament compound and a flexible, water-soluble film carrier therefor adapted for enteral or topical administration.

Belgian Patent Specification No. 637,363 describes paper films coated with pharmaceutically active medicinal compounds suitable for oral administration. The films comprise water-insoluble cellulose fibers and a water-soluble binding agent, preferably sodium carboxymethyl cellulose. In the examples thereof the pharmaceutically active compound is applied to the paper film by dripping a solution thereof onto the film, depositing the solid active compound on the surface thereof or by drawing the film through a solution of the active medicament. Using the film drawing machines prescribed in this patent, non-uniform layers of film are formed which shrink upon drying. In the alternative techniques described, the discontinuous process of separately making the film and applying the active medicament thereon has inherent disadvantages which prevent high accuracy in the dosages applied. This is of particular importance with the small doses of medicaments often employed in current pharmacy. Inaccuracies inherently arise not only in applying the active medicament, but also in the manufacture and pre-treatment of the carrier and in variations encountered during subsequent storage of the impregnated carrier material. As a non-uniform material is used as the carrier, the subsequent take-up of active medicament is also inherently non-uniform. Moreover, active medicaments bound only on the surface of the films can readily be removed therefrom during subsequent handling, e.g., in packaging. Furthermore, the carboxymethyl cellulose binding agent becomes detached in the stomach, liberating carboxymethyl cellulose from the carrier which entraps some of the active medicament and liberates it only very slowly, if at all.

OBJECTS OF THE INVENTION

Accordingly, it is a principal object of the present invention to provide improved medicament carriers in the form of a film having a pharmaceutically active compound uniformly incorporated therein.

Another object of the present invention is to provide such carriers which exhibit improved stability during subsequent handling.

A further object of the present invention is to provide such films having multiple pharmaceutical compositions uniformly incorporated therein, whereby incompatible substances can be stored on adjacent areas of the film without adversely interacting with each other.

An additional object of the present invention is to provide a method for the preparation of pharmaceutical compositions in unit dosage form employing a film or sheet carrier, which are adapted for enteral or topical administration.

Upon further study of the specification and appended claims, further objects and advantages of this invention will become apparent to those skilled in the art.

SUMMARY OF THE INVENTION

Briefly, the above and other objects are attained in one aspect of the present invention by providing a process for the manufacture of a pharmaceutical composition in unit dosage form adapted for enteral or topical administration and comprising a safe and effective amount of a pharmaceutically active medicament compound and a flexible, water-soluble film carrier therefor. In accordance with the present invention, the medicament is dissolved or uniformly suspended in a film-forming composition to form a homogeneous solution or dispersion which is then drawn with a film-drawing machine into a sheet, dried and then cut into any desired number and size of unit dosage forms.

DETAILED DISCUSSION

It has now been found that carrier films having a constant thickness and a uniformly homogeneous distribution of active medicament compounds can be obtained by preparing films having the active medicament incorporated therein and using film-forming compounds whch are soluble in water and/or polar, water-miscible organic solvents.

In principle, all pharmaceutically active medicaments used in human and veterinary medicine can be employed in accordance with the principles of the present invention. The dosages of active medicament employed are those conventionally used in the art for the particular medicament selected. For internal use, unit dosage forms adapted for oral administration are preferred. For external use, unit dosage forms adapted for either enteral or topical administration can be employed, e.g., for topical administration on the skin and in body cavities such as the nose, ears, rectum, vagina, etc.

Suitable pharmaceutically active medicament compounds which can be employed in accordance with the present invention include but are not limited to hormones, e.g., cyproterone acetate, progesterone, estradiol, testosterone, insulin, triiodthyronin, cortisone, etc.;

prostaglandins, e.g., prostaglandin $E_1$, prostaglandin $E_2$, prostaglandin $A_1$ and prostaglandin $F_{2\alpha}$;

vitamins, e.g., vitamin A, vitamin $D_2$, vitamin $D_3$, vitamin E, vitamin $K_1$, vitamin $K_2$ and derivatives of vitamin $B_1$, e.g., thiamine tetrahydrofurfuryl disulfide or thiamine propyldisulfide;

antibiotics, e.g., erythromycin and tetracycline;

contraceptives, e.g., chlormadinone, chlormadinone acetate, magestrol acetate, d-norgestrel, medroxyprogesterone acetate, norethisterone, norethisterone acetate, etc.;

and spermicides, e.g., p-diisobutylphenoxypolyethoxyethanol.

The drugs are employed in at least the pharmaceutically active amounts known in the art.

Of these, especially preferred medicinally active substances are the gestagens, estrogens and mixtures thereof, tranquilizers, anti-diabetics, sulfonamides, antibiotics, trichomonal agents, anti-inflammatory agents such as corticoids, etc.

Suitable films having a constant thickness and a uniform distribution of the medicinally active ingredients therein can be obtained by preparing films having the active medicament incorporated therein using film-forming polymers which are soluble in water or polar organic solvents, preferably film-forming polymers which are soluble both in water and in polar water-miscible organic solvents. Suitable such film-forming polymers are known in the art and include but are not limited to poly-N-vinyl-pyrrolidone, copolymers of vinylpyrrolidone and vinyl acetate, methyl-cellulose, ethyl-cellulose, etc.; preferably non-ionic, water-soluble, hydroxyalkyl ethers of cellulose and especially hydroxypropyl-cellulose, hydroxyethyl-cellulose and methylhydroxypropyl-cellulose.

As the films are formed by drawing in accordance with the present invention rather than by casting or by other known film-forming techniques, a release agent or parting compound is included in the composition to be drawn. Suitable release agents are likewise known in the art and include but are not limited to polyoxyethylene-polyoxypropylene copolymers, especially Pluronic F 68, polyoxyl stearates, alkyl- or alkanoyl-substituted polyaddition products of ethylene oxides, e.g., Cremophor EL, silicones and silicone parting emulsions, glycerine, propylene glycol, metal soaps, etc.

Suitable pharmaceutically acceptable fillers can also be employed if desired; such fillers are likewise known in the art and include but are not limited to cellulose; sugars, e.g., lactose, dextrose, cane sugar, etc.; starches; polyhydric alcohols, e.g., mannitol; inorganic fillers such as calcium carbonate, calcium phosphate, talc, etc.; and dyestuffs, either in soluble form or as pigments. The fillers are optional, and may be partially or wholly replaced by one or more pharmaceutically active substances. When using soluble fillers or pharmaceutically active substances, a transparent, smooth film is formed, while the use of insoluble fillers or active medicaments results in the formation of a white or colored, paper-like film.

The medicaments may be present in the carrier material either in a dissolved or uniformly suspended state. The proportion of pharmaceutically active ingredients in the film may be from a pharmaceutically effective trace amount up to about 60% by weight without deleteriously affecting the physical properties thereof. The drawn film surfaces can be cut or perforated to form simple single unit dosages which contain the customary active medicaments which have previously been used in the form of tablets, dragees, salves, suppositories, etc. Thus, the quantity of active medicament per single unit dose may be as high as desired depending on the mode of use, typically from about one microgram to 0.5 grams, but the lower and upper dosages may easily be reduced or increased. Of course, it is also possible to simultaneously form placebo carriers which otherwise correspond in composition to the unit dosage form of the present invention but are free of the medicament ingredient therein.

In preparing the unit dosage forms of the present invention, the medicament and a release agent (which may be omitted if the medicament employed itself has parting compound properties) are first dissolved or suspended in water and/or one or more polar organic solvents, preferably in admixture of water and a polar organic solvent which is miscible therewith or two organic solvents. The only criticality with respect to the choice of organic solvent is that it be relatively volatile so that only physiologically tolerable residues thereof are removed during the drawing step. Suitable such solvents are known in the art and include but are not limited to ethanol, isopropanol, acetone, methylene chloride, mixtures thereof, etc. Preferably, water, ethanol or mixtures thereof or mixtures of ethanol and methylene chloride are employed.

Into the solution or suspension of medicament and suspension medium is introduced about 6–20% by weight of the film-forming polymer, up to 30% by weight of a suitable filler, and preferably about 0.01–2% by weight of a release agent. The resultant admixture is rendered homogeneous by stirring or other suitable techniques, and the homogeneous solution or suspension is then drawn out on a film-drawing machine into a tissue-like sheet and dried. The film obtained upon drying the sheet is then divided into unit dosage sections. The layer thickness of the wet sheet is generally about 0.1–2 mm, while the layer thickness of the dry film is about 0.05–1 mm, preferably 0.07–0.3 mm.

The process of making the unit dosage forms of the present invention into a film in a single operation can be conducted continuously, and has the advantage that the medicament is homogeneously and uniformly distributed throughout the medicament carrier. By merely varying the concentration of the active medicament in the carrier, the thickness of the film and the area of the film employed per unit dosage, the amount of medicament per unit dose can be varied in an elegantly simple fashion.

A particular advantage of the present invention lies in the ability with which films can be prepared from a single sheet in which different pharmaceutically active medicaments and/or varying concentrations of active ingredients are incorporated side by side across the width of a drawn web. By using a doctor having two or more compartments during the drawing operation, different solutions or suspensions can be simultaneously drawn out into a coherent sheet without mixing the different ingredients. The width and thickness of the sheet can be adjusted separately for each compartment, providing a further measure of flexibility in the process of the present invention. If desired, the zones or strips having different active substances or different concentrations thereof can be visually identified by the use of different dyestuffs in each compartment. Upon drawing the wet sheet, a film is obtained which, by being suitably divided such as by simple perforation, can provide unit dosages containing different medicaments and/or different concentrations thereof, as well as placebos containing no medicament. Such films containing different medicaments and/or different concentrations thereof are widely used in modern pharmacology for making multi-phase preparations, such as contraceptive preparations. By providing a spatial separation of different medicaments which are storage-incompatible with each other on a single film unit, the shelf stability of each individual ingredient is greatly enhanced. Other applications will be readily apparent to those skilled in the art to which the invention pertains; for example, films for intravaginal application can simply be rolled about an ordinary commercial tampon for administration.

Without further elaboration, it is believed that one skilled in the art can, using the preceding description, utilize the present invention to its fullest extent. The following preferred specific embodiments are, therefore, to be construed as merely illustrative and not limitative of the remainder of the disclosure in any way whatsoever. In the following Examples, the temperatures are set forth uncorrected in degrees Celsius; unless otherwise indicated, all parts and percentages are by weight.

Pharmaceutical grade reagents as defined in the current DAB (Deutsches Arzneibuch) Pharmacopoeia were employed in the following Examples. With the exception of Examples 5 and 16, the preparations described by way of example are preponderantly suitable for oral administration.

EXAMPLE 1

Preparation for 1000 units
0.25 gram of d-norgestrel,
0.05 gram of ethinyl-estradiol and
0.84 gram of polyoxyethylene-polyoxypropylene copolymer are dissolved in
95.00 grams of ethyl alcohol with stirring, and into the resultant solution is homogeneously introduced a powdered mixture of
16.93 grams of hydroxypropyl-cellulose and
16.93 grams of cellulose The resultant suspension is drawn on a suitable film drawing apparatus to a sheet having a thickness of 500 μm, and is then dried.

The composition of one unit:
0.25 mg. of d-norgestrel
0.05 mg. of ethinyl-estradiol
0.84 mg. of polyoxyethylene-polyoxypropylene copolymer
16.93 mg. of hydroxypropyl-cellulose
16.93 mg. of cellulose
35.00 mg.
One unit corresponds to an area of about 3 cm$^2$.
Appearance of the film: white, paper-like.
The dry film has a thickness of about 170 μm.

EXAMPLE 2

A preparation for 1000 units
1.10 grams of Cremophor EL® are dissolved in
152.00 grams of water. In this solution are homogeneously suspended
0.25 gram of micronized d-norgestrel and
0.05 gram of micronized ethinyl-estradiol. Into the suspension are introduced
22.10 grams of hydroxypropyl-cellulose and
16.50 grams of cellulose.

The suspension so obtained is drawn on a suitable film drawing apparatus to a sheet having a thickness of 500 μm, and is then dried.

The composition for one unit:
0.25 mg. of d-norgestrel
0.05 mg. of ethinyl-estradiol
1.10 mg. of Cremophor EL®
22.10 mg. of hydroxypropyl-cellulose
16.50 mg. of cellulose
40.00 mg.
One unit corresponds to an area of about 3 cm$^2$.
Appearance of the film: white, paper-like.
The dry film has a thickness of about 170 μm.

EXAMPLE 3

A preparation for 1000 units
0.03 gram of d-norgestrel and
0.84 gram of polyoxyl-40-stearate are dissolved, while stirring, in
95.00 grams of ethyl alcohol. Into this solution is introduced a powdered mixture of
16.93 grams of hydroxypropyl-cellulose and
17.20 grams of cellulose.

The suspension so obtained is drawn by a suitable film drawing apparatus onto a sheet having a thickness of 500 μm, and is then dried.

The composition of one unit:
0.03 mg. of d-norgestrel
0.84 mg. of polyoxyl-40-stearate
16.93 mg. of hydroxypropyl-cellulose
17.20 mg. of cellulose
35.00 mg.
One unit corresponds to an area of about 3 cm$^2$.
Appearance of the film: white, paper-like.
The dry film has a thickness of about 170 μm.

EXAMPLE 4

A preparation for 1000 units
1.10 grams of polyoxyethylene-polyoxypropylene copolymer are dissolved in
152.00 grams of demineralized water. In this solution is suspended
0.03 gram of micronized d-norgestrel to form a homogeneous suspension. Into the suspension are introduced
22.10 grams of hydroxypropyl-cellulose and
16.77 grams of cellulose.

The suspension so obtained is drawn on a suitable film drawing apparatus to a sheet having a thickness of 500 μm, and is then dried.

The composition for one unit:
0.03 mg. of d-norgestrel
1.10 mg. of polyoxyethylene-polyoxypropylene copolymer
22.10 mg. of hydroxypropyl-cellulose
16.77 mg. of cellulose
40.00 mg.
One unit corresponds to an area of about 3 cm$^2$.
Appearance of the film: white, paper-like.
The dry film has a thickness of about 170 μm.

EXAMPLE 5

A preparation for 1000 units
0.025 gram of fluocortolone trimethylacetate and
0.183 gram of glycerine are dissolved in
30.000 grams of ethyl alcohol. Into this solution are introduced
7.292 grams of hydroxypropyl-cellulose.

The solution so obtained is drawn on a suitable film drawing apparatus to a sheet having a thickness of 500 μm, and is then dried.

The composition of one unit:
0.025 mg. of fluocortolone trimethylacetate
0.183 mg. of glycerine
7.292 mg. of hydroxypropyl-cellulose
7.500 mg.
One unit corresponds to an area of about 1 cm$^2$.
Appearance of the film: transparent.
The dry film has a thickness of about 70 μm.
The film is suitable for topical use.

EXAMPLE 6

A preparation for 1000 units
10.00 grams of 7-chloro-2-methylamino-5-phenyl-3H-1,4-benzo-diazepine-4-oxide and
0.84 gram of polyoxyethylene-polyoxypropylene copolymer are dissolved in
95.00 grams of ethyl alcohol. Into this solution is introduced a powdered mixture of
16.93 grams of hydroxypropyl-cellulose and
7.23 grams of cellulose.

The suspension so obtained is drawn on a suitable film drawing apparatus to a sheet having a thickness of 500 μm, and is then dried.

The composition of one unit:
10.00 mg. of 7chloro-2-methylamino-5-phenyl-3H-1,4-benzo-diazepine-4-oxide
0.84 mg. of polyoxyethylene-polyoxypropylene copolymer
16.93 mg. of hydroxypropyl-cellulose
7.23 mg. of cellulose
35.00 mg.

One unit corresponds to an area of about 3 cm$^2$.
Appearance of the film: yellow, paper-like.
The dry film has a thickness of about 170 μm.

EXAMPLE 7

A preparation for 1000 units
1.00 gram of norethisterone acetate,
0.03 gram of ethinyl-estradiol and
0.84 gram of polyoxyethylene-polyoxypropylene copolymer are dissolved in
95.00 grams of ethyl alcohol. Into this solution is introduced a powdered mixture of
16.93 grams of hydroxypropyl-cellulose and
16.20 grams of cellulose.

The suspension so obtained is drawn on a suitable film drawing apparatus to a sheet having a thickness of 500 μm, and is then dried.

The composition for one unit:
1.00 gm. of norethisterone acetate
0.03 mg. of ethinyl-estradiol
0.84 mg. of polyoxyethylene-polyoxypropylene copolymer
16.93 mg. of hydroxypropyl-cellulose
16.20 mg. of cellulose
35.00 mg.

One unit corresponds to an area of about 3 cm$^2$.
Appearance of the film: white, paper-like.
The dry film has a thickness of about 170 μm.

EXAMPLE 8

A preparation for 1000 units
1.00 gram of norethisterone acetate,
0.03 gram of ethinyl-estradiol and
0.84 gram of propylene glycol are dissolved in a mixture of
101.60 grams of methylene chloride and
26.40 grams of ethyl alcohol. Into this solution is introduced a powdered mixture of
8.47 grams of hydroxypropyl-cellulose,
8.47 grams of hydroxyethyl-cellulose and
16.19 grams of cellulose.

The suspension so obtained is drawn on a suitable film drawing apparatus to a sheet having a thickness of 500 μm, and is then dried.

The composition for one unit:
1.00 mg. of noresthisterone acetate
0.03 mg. of ethinyl-estradiol
0.84 mg. of propylene glycol
8.47 mg. of hydroxypropyl-cellulose
8.47 mg. of hydroxyethyl-cellulose
16.19 mg. of cellulose
35.00 mg.

One unit corresponds to an area of about 3 cm$^2$.
Appearance of the film; white, paper-like.
The dry film has a thickness of about 170 μm.

EXAMPLE 9

A preparation for 1000 units
1.00 gram of noresthisterone acetate,
0.03 gram of ethinyl-estradiol and
0.84 gram of polyoxyethylene-polyoxypropylene copolymer are dissolved in
101.60 grams of methylene chloride and
25.40 grams of ethyl alcohol. Into this solution is introduced a powdered mixture of
16.93 grams of hydroxyethyl-cellulose and
16.20 grams of starch.

The suspension so obtained is drawn on a suitable film drawing apparatus to a sheet having a thickness of 500 μm, and is then dried.

The composition for one unit;
1.00 mg. of norethisterone acetate
0.03 mg. of ethinyl-estradiol
0.84 mg. of polyoxyethylene-polyoxypropylene copolymer
16.93 mg. of hydroxyethyl-cellulose and
16.20 mg. of starch
35.00 mg.

One unit corresponds to an area of about 3 cm$^2$.
Appearance of the film; white, paper-like.
The dry film has a thickness of about 170 μm.

EXAMPLE 10

A preparation for 1000 units
1.00 gram of norethisterone acetate,
0.03 gram of ethinyl-estradiol and
0.84 gram of polyoxyl-40-stearate are dissolved in
95.00 grams of ethyl alcohol. Into this solution is introduced a powdered mixture of
16.93 grams of hydroxypropyl-cellulose,
8.10 grams of lactose and
8.10 grams of maize starch.

The suspension so obtained is drawn on a suitable film drawing apparatus to a sheet having a thickness of 500 μm, and is then dried.

The composition for one unit:
1.00 mg. of norethisterone acetate
0.03 mg. of ethinyl-estradiol
0.84 mg. of polyoxyl-40-stearate
16.93 mg. of hydroxypropyl-cellulose
8.10 mg. of lactose
8.10 mg. of maize starch
35.00 mg.

One unit corresponds to an area of about 3 cm$^2$.
Appearance of the film: white, paper-like.
The dry film has a thickness of about 170 μm.

EXAMPLE 11

A preparation for 1000 units
1.00 gram of norethisterone (17α-ethinyl-19-nor-testosterone
0.03 gram of ethinyl-estradiol and
0.22 gram of polyoxyethylene-polyoxypropylene copolymer are dissolved in a mixture of
84.75 grams of ethyl alcohol and
4.00 grams of water. Into this solution is introduced a powdered mixture of
16.00 grams of hydroxypropyl-cellulose and
16.00 grams of cellulose.

The suspension so obtained is drawn on a suitable film drawing apparatus to a sheet having a thickness of 600 μm, and then dried.

The composition for one unit:

1.00 mg. of norethisterone (17α-ethinyl-19-nor-testosterone)
0.03 mg. of ethinyl-estradiol
0.22 mg. of polyoxyethylene-polyoxypropylene copolymer
16.00 mg. of hydroxypropyl-cellulose
16.00 mg. of cellulose
33.25 mg.

One unit corresponds to an area of about 3 cm².
Appearance of the film: white, paper-like.
The dry film has a thickness of approximately 230 μm.

EXAMPLE 12

A preparation for 1000 units
4.0 grams of glisoxepide* in micronized form are suspended in
0.9 gram of polyoxyl-40-stearate dissolved in
152.0 grams of water to form a homogeneous suspension. Into the suspension are introduced
15.0 grams of hydroxyethyl-cellulose and
15.1 grams of calcium carbonate.

The suspension so obtained is drawn on a suitable film drawing apparatus to a sheet having a thickness of 500 μm and dried.

The composition for one unit:
4.00 mg. of glisoxepide*
0.90 mg. of polyoxyl-40-stearate
15.00 mg. of hydroxyethyl-cellulose
15.10 mg. of calcium carbonate
35.00 mg.

One unit corresponds to an area of about 3 cm².
Appearance of the film: white, paper-like.
The dry film has a thickness of about 170 μm. *Glisoxepide is 4-{4-[β-(5-methyl-isoxazol-3-carboxamido)-ethyl]-benzolsulfonyl}-1,1-hexamethylene-semicarbazide.

EXAMPLE 13

A preparation for 1000 units
0.030 gram of d-norgestrel is dissolved in
40.000 grams of methylene chloride and
55.000 grams of ethanol. Into this solution are introduced
0.840 gram of silicone oil
6.930 grams of methyl-cellulose and
10.000 grams of poly-N-vinyl-pyrrolidone and
17.200 grams of starch to form a homogeneous suspension.

The suspension so obtained is drawn on a suitable film drawing apparatus to a sheet having a thickness of 500 μm and dried.

The composition of one unit:
0.030 mg. of d-norgestrel
0.840 mg. of silicone oil
6.930 mg. of methyl-cellulose
10.000 mg. of poly-N-vinyl-pyrrolidone
17.200 mg. of starch
35.000 mg.

One unit corresponds to an area of about 3 cm².
Appearance of the film: white, paper-like.
The dry film has a thickness of about 170 μm.

EXAMPLE 14

A preparation for 1000 units
0.84 grams of polyoxyethylene-polyoxypropylene copolymer is dissolved in
95.00 grams of ethyl alcohol while stirring, and into this solution is introduced a powdered mixture of
17.08 grams of hydroxypropyl-cellulose and
17.08 grams of cellulose.

The suspension so obtained is drawn on a suitable film drawing apparatus to a sheet having a thickness of 500 μm, and then dried.

The composition for one unit:
0.84 mg. of polyoxyethylene-polyoxypropylene copolymer
17.08 mg. of hydroxypropyl-cellulose
17.08 mg. of cellulose
35.00 mg.

EXAMPLE 15

A preparation for 1000 units
0.04 gram of saccharin,
0.04 gram of cream essence and
0.40 gram of polyoxyethylene-polyoxypropylene copolymer are dissolved in a mixture of
79.00 grams of ethyl alcohol and
4.00 grams of water. Into this solution are introduced
30.00 grams of iron(II) fumarate,
15.00 grams of hydroxypropyl-cellulose,
5.52 grams of cocoa and
4.00 grams of cellulose to form a homogeneous mixture.

The suspension so obtained is drawn on a suitable film drawing apparatus to a sheet having a thickness of 0.5mm, and then dried.

The composition for one unit:
30.00 mg. of iron(II) fumarate
15.00 mg. of hydroxypropyl-cellulose
4.00 mg. of cellulose
0.40 mg. of polyoxyethylene-polyoxypropylene copolymer
5.52 mg. of cocoa
0.04 mg. of saccharin
0.04 mg. of cream essence
55.00 mg. Weight per unit.

One unit corresponds to an area of about 3 cm².
Appearance of the film: pale red-brown.

EXAMPLE 16

Films for intravaginal application: The film is prepared in accordance with Example 11.
The composition of one unit:
100.0 mg. of 5-morpholinomethyl-3-(5-nitro-1-methyl-2-imidazolyl)-methyleneamino-2-oxazolidinone.HCl
8.4 mg. of Cremophor EL ®
169.2 mg. of methylhydroxypropyl-cellulose
72.4 mg. of cellulose
350.0 mg. Weight of one unit.

One unit corresponds to an area of about 8 × 4 cm.
Appearance of the film: pale yellow.
The film (1 unit) is either rolled around an ordinary commercial tampon or is itself rolled to form a narrow tube.

EXAMPLE 17

This Example demonstrates the simplicity of a two-phase preparation in accordance with the present invention.
Part A: 21 units containing active substance.
Part B: 7 units without active substance (placebo).
Preparation for 3000 units, Part A.
0.75 gram of d-norgestrel, 0.15 gram of ethinyl-estradiol and
0.54 gram of polyoxyethylene-polyoxypropylene copolymer are dissolved in a mixture of
237.00 grams of ethyl alcohol and
12.00 grams of water. Into this solution are introduced
44.28 grams of hydroxypropyl-cellulose and
44.28 grams of cellulose to form a homogeneous suspension.
Preparation for 1000 units, Part B.
0.18 gram of polyoxyethylene-polyoxypropylene copolymer is dissolved in a mixture of
79.00 grams of ethyl alcohol and
4.00 grams of water. Into this solution are introduced
14.91 grams of hydroxypropyl-cellulose and
14.91 grams of cellulose to form a homogeneous suspension.

The suspensions so obtained are drawn on a suitable film drawing apparatus having a two compartment doctor (widths of the compartments: #1 = 54 mm; #2 = 18 mm) to form a sheet of 0.5 mm and then dried. By appropriate division into units measuring 18 × 18 mm, e.g., by perforation, the film can be divided over its width into three units containing active substance and one placebo unit free of active substance. There may be produced in the web of film any desired number of sections having a ratio of three units containing active substance to one placebo unit containing no active substance.

The composition of each unit:

| Part A (containing active substance). | Part B (placebo). |
|---|---|
| 0.25 mg. of d-norgestrel | — |
| 0.05 mg. of ethinyl-estradiol | — |
| 14.76 mg. of hydroxypropyl-cellulose | 14.91 mg. |
| 14.76 mg. of cellulose | 14.91 mg. |
| 0.18 mg. of polyoxyethylene-polyoxypropylene copolymer | 0.18 mg. |
| 30.00 mg. | 30.00 mg. |
| Area per unit: about 3 cm$^2$. | |
| Appearance: white. | |

EXAMPLE 18

This Example demonostrates the ease of making a three-phase preparation containing two active substance phases and a placebo in accordance with the present invention.

Part A: 11 units containing 0.05 mg. of d-norgestrel 0.05 mg. of ethinyl-estradiol.
Part B: 10 units containing 0.125 mg. of d-norgestrel 0.050 mg. of ethinyl-estradiol.
Part C: 7 placebo units without active substance.
Preparation for 1100 units, Part A.
0.055 gram of d-norgestrel,
0.055 gram of ethinyl-estradiol and
0.198 gram of polyoxyethylene-polyoxypropylene copolymer are dissolved in a mixture of
86.900 grams of ethyl alcohol and
4.400 grams of water. Into this solution are introduced
16.346 grams of hydroxypropyl-cellulose and
16.346 grams of cellulose to form a homogeneous suspension.
Preparation for 1000 units, Part B.
0.125 gram of d-norgestrel,
0.050 gram of ethinyl-estradiol and
0.180 gram of polyoxyethylene-polyoxypropylene copolymer are dissolved in a mixture of
79.000 grams of ethyl alcohol and
4.000 grams of water. Into this solution are introduced
14.823 grams of hydroxypropyl-cellulose and
14.823 grams of cellulose to form a homogeneous suspension.
Preparation for 700 units, Part C.
0.189 gram of polyoxyethylene-polyoxypropylene copolymer is dissolved in a mixture of
82.950 grams of ethyl alcohol and
4.200 grams of water. Into this solution are introduced
15.656 grams of hydroxypropyl-cellulose and
15.655 grams of cellulose to form a homogeneous suspension.

The suspensions so obtained are drawn on a suitable film drawing apparatus having a three compartment doctor (width per compartment 18 mm) into a sheet and dried. By appropriate division, e.g., by perforation, there can be distributed over the width of the film three units of 18 × 18 mm for Part A, of 18 × 19.8 mm for Part B and of 18 × 28 mm for Part C, each having different contents of active substance. There can be separated from the film web preparations having 11 units of Part A, 10 units of part B and 7 units of Part C.

The composition per unit:

| Part A | Part B | Part C | Ingredients |
|---|---|---|---|
| 0.050 mg. | 0.125 mg. | — | d-norgestrel |
| 0.050 mg. | 0.050 mg. | — | ethinyl-estradiol |
| 0.180 mg. | 0.180 mg. | 0.270 mg. | polyoxyethylene-polyoxypropylene copolymer |
| 14.860 mg. | 14.823 mg. | 22.366 mg. | hydroxypropyl-cellulose |
| 14.860 mg. | 14.822 mg. | 22.364 mg. | cellulose |
| 30.000 mg. | 30.000 mg. | 45.000 mg. | weight per unit |
| about 3 cm$^2$ | about 3.5 cm$^2$ | about 5 cm$^2$ | area per unit |
| white | white | white | appearance |

EXAMPLE 19

The various phases need not contain the same pharmaceutically active ingredients, as is shown by the following three-phase preparation.

Part A: 11 units containing 0.05 mg. of d-norgestrel 0.05 mg. of ethinyl-estradiol
Part B: 10 units containing 0.125 mg. of d-norgestrel 0.050 mg. of ethinyl-estradiol
Part C: 7 units containing 50.00 mg. of iron(II) fumarate.
Preparation for 1100 units, Part A.
0.066 gram of food color yellow No. 2 (tartrazine; E 102) is dissolved in
4.400 grams of water, and then introduced into
86.900 grams of ethyl alcohol. In this solution are dissolved
0.055 gram of d-norgestrel,
0.055 gram of ethinyl-estradiol and
0.198 gram of polyoxyethylene-polyoxypropylene copolymer. Into this solution are introduced
16.313 grams of hydroxypropyl-cellulose and
16.313 grams of cellulose to form a homogeneous suspension.
Preparation for 1000 units, Part B.
0.065 gram of food color orange No. 2 (Sunset Yellow; E 110) is dissolved in
4.000 grams of water, and then introduced into 79.000 grams of ethyl alcohol. In this solution are dissolved
0.125 gram of d-norgestrel,
0.050 gram of ethinyl-estradiol and
0.180 gram of polyoxyethylene-polyoxypropylene copolymer. Into this solution are introduced
14.790 grams of hydroxypropyl-cellulose and
14.790 grams of cellulose to form a homogeneous suspension.
Preparation for 700 units, Part C.
0.042 gram of saccharin,
0.042 gram of cream essence and
0.406 gram of polyoxyethylene-polyoxypropylene copolymer are dissolved in a mixture of
55.300 grams of ethyl alcohol and
2.800 grams of water. Into this solution are introduced
35.000 grams of iron(II) fumarate,
17.500 grams of hydroxypropyl-cellulose,
5.950 grams of cocoa and
4.060 grams of cellulose to form a homogeneous suspension.

The suspensions so prepared are drawn on a suitable film drawing apparatus having a three compartment doctor (width per compartment 18 mm) into a sheet and dried. By appropriate division, e.g., by perforation, there can be distributed over the width of the film three units of 18 × 18 mm for Part A, of 18 × 19.8 mm for Part B and of 18 × 28 mm for Part C, each having different contents of active substance. There can be separated from the film web preparations having 11 units of Part A, 10 units of Part B and 7 units of Part C.

The composition per unit:

| Part A | Part B | Part C | Ingredients |
|---|---|---|---|
| 0.050 mg. | 0.125 mg. | — | d-norgestrel |
| 0.050 mg. | 0.050 mg. | — | ethinyl-estradiol |
| — | — | 50.000 mg. | iron(II) fumarate |
| 0.180 mg. | 0.180 mg. | 0.580 mg. | polyoxyethylene-polyoxypropylene copolymer |
| 0.060 mg. | — | — | food color Yellow No. 2 |
| — | 0.065 mg. | — | food color Orange No. 2 |
| 14.830 mg. | 14.790 mg. | 25.000 mg. | hydroxypropyl-cellulose |
| 14.830 mg. | 14.790 mg. | 5.800 mg. | cellulose |
| — | — | 8.500 mg. | cocoa |
| — | — | 0.060 mg. | saccharin |
| — | — | 0.060 mg. | cream essence |
| 30.000 mg. | 30.000 mg. | 90.000 mg. | weight per unit |
| about 3 cm$^2$ | about 3.5 cm$^2$ | about 5 cm$^2$ | area per unit |
| yellow | yellow | brown | appearance |

EXAMPLE 20

Preparation for 1000 units
0.15 gram of d-norgestrel,
0.03 gram of ethinyl-estradiol and
0.84 gram of polyoxyethylene-polyoxypropylene copolymer are dissolved in
95.00 grams of ethyl alcohol while stirring and a powdered mixture of
16.99 grams of hydroxypropyl-cellulose and
16.99 grams of cellulose is introduced into this solution.

The suspension obtained is drawn out on a suitable film drawing apparatus to a very thin film having a thickness of 500 μm, and is then dried.

The composition of one unit:
0.15 mg. of d-norgestrel
0.03 mg. of ethinyl-estradiol
0.84 mg. of polyoxyethylene-polyoxypropylene copolymer
16.99 mg. of hydroxypropyl-cellulose
16.99 mg. of cellulose
35.00 mg.

One unit corresponds to an area of approximately 3 cm$^2$.

Appearance of the film: white, paper-like.
The dry film has a thickness of approximately 170 μm.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. In a pharmaceutical composition in unit dosage form for enteral or topical administration and comprising a safe and a pharmaceutically effective amount of an active medicament compound and a flexible, water soluble film carrier therefor, the improvement wherein: the medicament is dissolved or uniformly suspended in a film carrier consisting essentially of a non-ionic, water soluble methyl ether or hydroxyalkyl ether of cellulose and the pharmaceutical composition is in the form of a tissue-like sheet, having a uniform dry film thickness of about 0.05–1 mm., drawn from a solution of the film carrier containing 0–30% by weight of a filler and up to 60% by weight of the film carrier of the medicament.

2. A composition according to claim 1, wherein the film carrier is hydroxypropyl-cellulose, hydroxyethyl-cellulose, methylhydroxypropyl-cellulose or a mixture thereof.

3. A composition according to claim 1, wherein the medicament is an estrogen, gestagen or admixture thereof.

4. A composition according to claim 1, wherein the release agent is a polyoxethylene-polyoxypropylene copolymer, a polyoxylstearate or an alkyl- or alkanoyl-substituted polyaddition product of ethylene oxide.

5. A composition according to claim 1 wherein the medicament or concentration thereof differs in areas thereof defined by strips adjacent to one another along the width of the sheet.

6. A composition according to claim 5, wherein the strips are identified by different dyestuffs.

7. A composition according to claim 1, wherein the sheet is perforated to provide a plurality of single-unit dosages.

8. A composition according to claim 1, wherein the sheet is a transparent and smooth film.

9. A composition according to claim 1 containing a water-insoluble filler uniformly suspended in the film carrier and the film is paper-like.

10. A composition according to claim 9, wherein the filler is cellulose.

11. A composition according to claim 1, wherein the film carrier is methyl cellulose.

12. A composition according to claim 1, wherein the sheet has a thickness of 0.07–0.3 mm.

13. A composition according to claim 1, wherein the film carrier is hydroxypropyl-cellulose, hydroxyethyl-cellulose, methylhydroxypropyl-cellulose or a mixture thereof; the medicament is an estrogen, gestagen or admixture thereof; the release agent is a polyoxethylene-polyoxypropylene copolymer, a polyoxyl stearate or an alkyl- or alkanoyl-substituted polyaddition product of ethylene oxide; and the sheet has a thickness of 0.07–0.3 mm.

14. A pharmaceutical composition in unit dosage form for enteral or topical administration and comprising a safe and a pharmaceutically effective amount of an active medicament compound and a flexible, water soluble film carrier therefor, prepared by a process which comprises:

(a) drawing into a sheet having a uniform layer thickness of about 0.1–2 mm and a dry thickness of about 0.05–1 mm, a homogeneous solution or suspension consisting essentially of (1) up to 60% by weight, based on the film carrier, of the medicament, (2) 0–30% by weight of a pharmaceutically acceptable filler, (3) a film-forming amount of a water-soluble film-forming polymer, and (4) as solvent or suspending medium, one or both of water and an organic volatile solvent system comprising an organic polar solvent miscible in water; and (b) drying the thus-formed sheet to remove the solvent or suspending medium therefrom.

15. The pharmaceutical composition of claim 14, wherein the homogeneous solution or suspension additionally contains about 0.01–2% by weight of a pharmaceutically acceptable release agent.

16. The pharmaceutical composition of claim 1 wherein the solution of the film carrier additionally contains 0.01–2% by weight of a pharmaceutically acceptable release agent.

* * * * *